(12) United States Patent
Wakita et al.

(10) Patent No.: US 7,471,603 B2
(45) Date of Patent: Dec. 30, 2008

(54) OPTICAL ANALYZER

(75) Inventors: Tsugio Wakita, Matsuyama (JP);
Toshiki Matsumoto, Matsuyama (JP)

(73) Assignee: Panasonic Corporation, Osaka (JP)

( * ) Notice: Subject to any disclaimer, the term of this patent is extended or adjusted under 35 U.S.C. 154(b) by 633 days.

(21) Appl. No.: 11/195,767

(22) Filed: Aug. 3, 2005

(65) Prior Publication Data
US 2006/0028955 A1 Feb. 9, 2006

(30) Foreign Application Priority Data
Aug. 6, 2004 (JP) ............................. 2004-230006

(51) Int. Cl.
*G11B 7/00* (2006.01)
(52) U.S. Cl. ............... 369/53.31; 369/53.12; 369/47.44
(58) Field of Classification Search ................ 369/53.1, 369/44.41, 44.42, 124.12, 112.12, 53.12, 369/53.31, 47.44, 120, 121
See application file for complete search history.

(56) References Cited

U.S. PATENT DOCUMENTS 7,079,468 B2 * 7/2006 Worthington et al. ......... 369/94

FOREIGN PATENT DOCUMENTS

WO   WO 96/09548   3/1996

\* cited by examiner

*Primary Examiner*—Nabil Z Hindi
(74) *Attorney, Agent, or Firm*—Steptoe & Johnson LLP

(57) ABSTRACT

There is provided an apparatus capable of switching between a laser that emits light having a wavelength suitable for detecting samples and a laser required for reading traced data, while an analysis optical disc is being traced. In an analyzer in which an analysis disc having a sample to be analyzed which is located in a part of its track is irradiated with laser light to read the state of the sample, a selector switch alternately selects a laser having a wavelength for reading data represented by bits or wobble grooves on the disc and a laser having a wavelength suitable for detecting a sample, in response to an instruction from a control unit.

16 Claims, 12 Drawing Sheets

F I G. 2
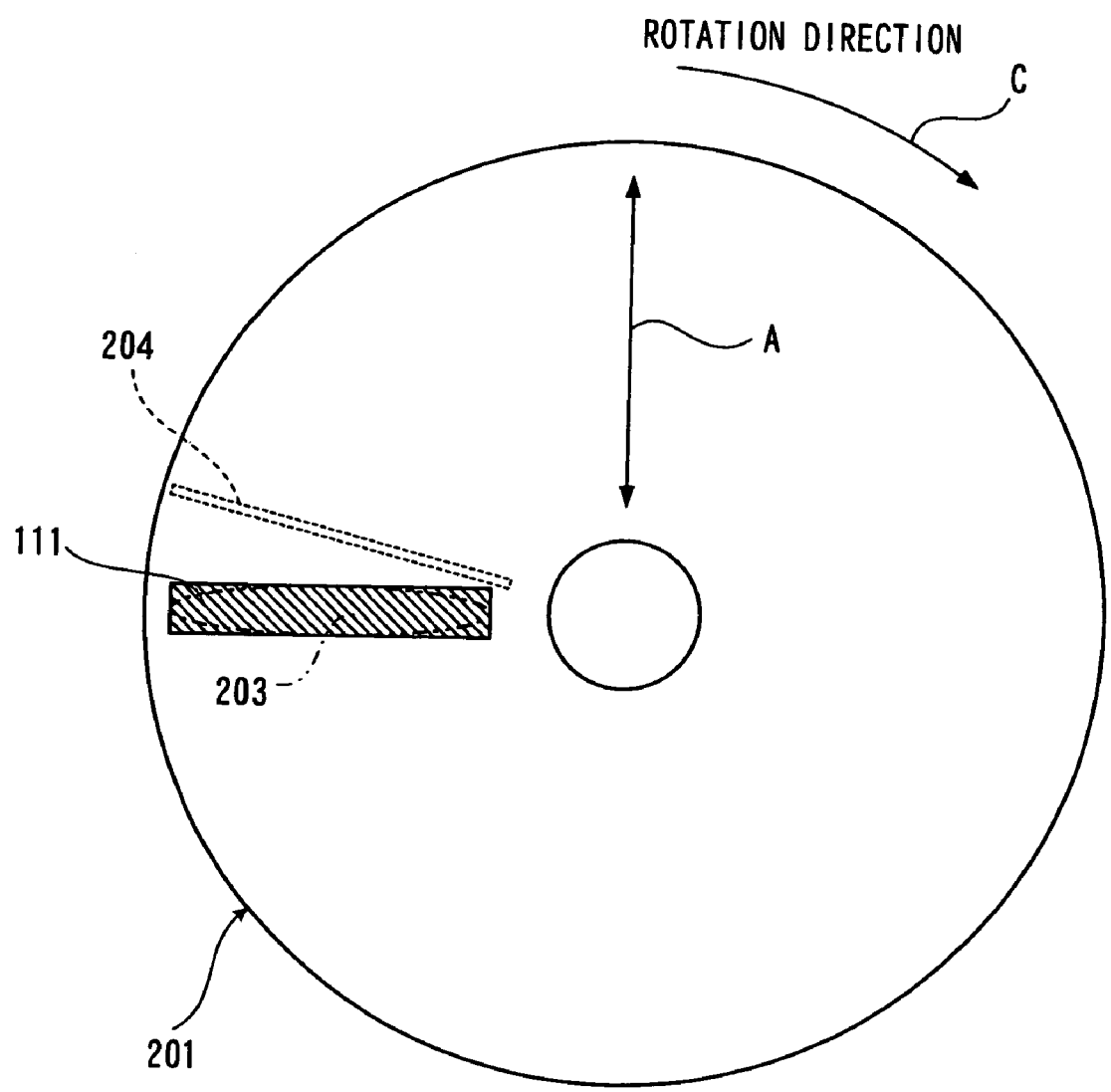

F I G. 3
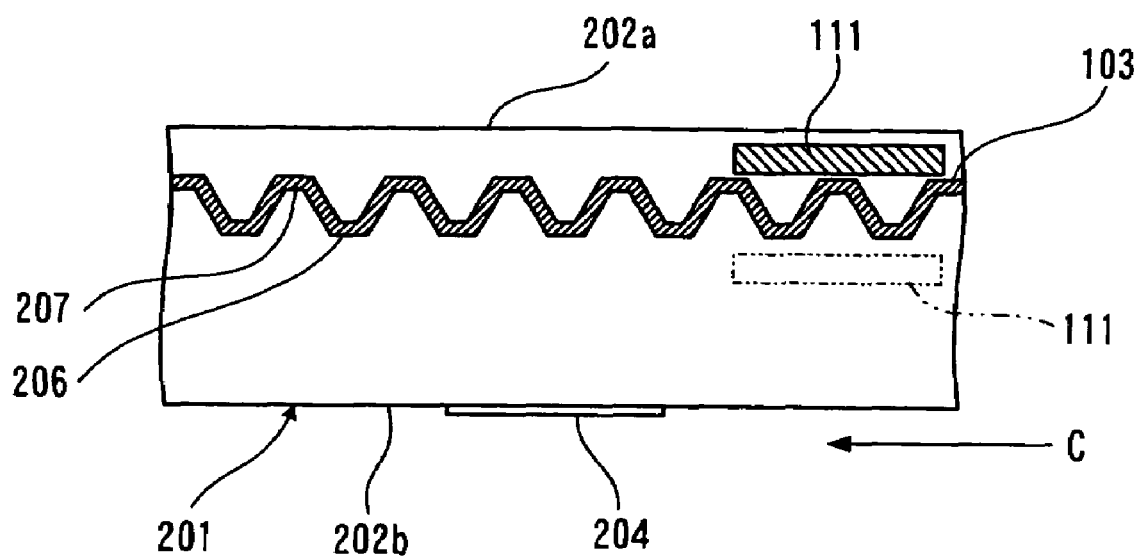

FIG. 9A ANALYSIS TRIGGER SIGNAL 14
FIG. 9B SECOND LASER DRIVE SIGNAL 9a
FIG. 9C SECOND LASER OUTPUT MONITORING SIGNAL 11a
FIG. 9D THIRD LASER DRIVE SIGNAL 9b
FIG. 9E THIRD LASER OUTPUT MONITORING SIGNAL 11b

OPTICAL ANALYZER

FIELD OF THE INVENTION

The present invention relates to an optical analyzer for performing optical inspections on biological, chemical, or biochemical samples by using an optical scanning function of an optical disc device.

BACKGROUND OF THE INVENTION

Some conventional optical-disc-based optical analyzers use a playback function of an optical disc device to trace a sample under test provided on a certain part of an optical disc by using a laser to obtain an image of the traced sample. (See Japanese Unexamined Patent Publication No. 10-504397, for example.)

An optical disc 101 has a track 103 in an aluminum reflecting layer formed on the surface of a substrate 102 and information is recorded on the track 103 as microscopic pits or wobble grooves 104, as shown in FIGS. 10 and 11. Reference numeral 105 indicates a protective layer.

In conventional optical disc units, information on a track 103 is read by using laser light Ph from a pick-up 107 while the optical disc 101 is being rotated in the direction indicated by arrow C by a disc motor 106 as shown in FIG. 12. The pick-up 107 engages a lead screw 109 which is driven by a traverse motor 108. A servo control circuit 110 drives the traverse motor 108 to move the pick-up 107 radially according to reproduction outputs from the pick-up 107 so that the pick-up follows and traces the track 103. The servo control circuit 110 also detects address information recorded on the track 103 and CLV-controls (Constant-Linear-Velocity-controls) the disc motor 106 so that a constant linear velocity is maintained.

More specifically, the position irradiated with the laser light Ph on the optical disc 101 is controlled by the traverse motor 108 and the light path of the laser light Ph is also controlled in the direction of the surface of the optical disc 101 by a tracking actuator (not shown) provided inside the pick-up 107 as required so that the track 103 is accurately traced.

The configuration described so far is the same as that of typical optical disc units for conventional audio or video optical discs. Unlike audio and video discs, an analyzing optical disc 101 has a sample 111 provided on it as shown in FIGS. 10 and 11. Optical analyzers have a photodetector (hereinafter referred to as PD) provided in the pick-up 107, in addition to the components of the optical disc unit for audio or video optical discs, which reads light reflected from the sample 111. The reflected light is processed by a video signal processing circuit 112 to obtain the image of the sample 111.

In the example described above, light reflected from an optical disc 101 is read and analyzed. If a sample 111 is to be analyzed by observing light transmitted through the optical disc, the PD is provided above the optical disc 101.

In such an optical analyzer, a laser with the same wavelength outputted from the optical pick-up 107 is used for both reading the track and analyzing a sample. Because a laser emitted from a single light source is used and the information recorded as pits or wobble grooves on the disc must be accurately read and traced, the laser used for analysis cannot be adjusted so as to emit light having a wavelength other than the wavelength for reading the pits or wobbles on the disc.

The inventers have been conducting studies and found that a laser wavelength (780 nm) for detecting pits and wobble grooves is not necessarily most suitable for capturing the image or light and shade of a part in which a sample is provided.

For example, if absorptiometric analysis is used for analyzing samples, it is advantageous to use the maximum absorption wavelength of the samples to be analyzed. Therefore, a light source is needed that can generate a wide range of wavelengths in order to conduct analysis of various types of samples on a single analyzer. For example, potassiumpermanganate solutions absorb light of wavelengths between 525 to 545 nm best. That is, they are the maximum absorption wavelengths for the solutions. In that case, almost all light with a wavelength of 700 nm pass through these solutions.

A water soluble formazan commonly called WST-3 (manufactured by DOJINDO laboratories), which is generated from a tetrazolium salt reduced by NADH exhibits the highest absorbance at a maximum absorption wavelength of 433 nm. Also this solution absorbs almost no light having wavelengths of 600 nm or more. Therefore, it is disadvantageous for high-precision measurement to use a single wavelength to conduct absorption analysis of different substances having different absorption spectra.

The turbidity of a sample can be cancelled by using the difference between the absorbance of the sample at its maximum absorption wavelength and the absorbance at a wavelength substantially different from the wavelength. However, under present circumstances, analysis in which turbidities are canceled cannot be conducted because present-day optical analyzers can output only a single laser wavelength.

An object of the present invention is to provide an optical analyzer suitable for obtaining information from pits or wobble grooves on an optical disc as well as for obtaining the image of a sample portion and detecting calorimetric information about the sample, such as light and shade or the absorbance of the sample.

DISCLOSURE OF THE INVENTION

According to the first aspect of the present invention, there is provided an optical analyzer for optically analyzing a sample located on a part of an analysis disc while rotating the analysis disc, the analysis disc having a track on which address information is recorded, the optical analyzer including a reading diode emitting laser light for reading data concerning address information on the track of the analysis disc, an analyzing diode emitting to the sample laser light with a wavelength different from the wavelength of laser light emitted by the reading diode, a first photodetector for reading light emitted from the reading diode or the analyzing diode and reflected by or transmitted through the analysis disc, and a second photodetector for reading light emitted from the reading diode or the analyzing diode and reflected by the analysis disc, wherein position control of the reading diode and the analyzing diode in the direction of the radius of the analysis disc is performed according to reading output from the second photodetector (PD2), and a result of analysis of the sample is read from reading output from the first photodetector.

According to the second aspect of the present invention, the optical analyzer according to the first aspect is provided, wherein a final result of analysis of a same sample is provided based on a result of analysis of light which is emitted from the reading diode, reflected by or transmitted through the analysis disc and read by the first photodetector, and on a result of analysis of light emitted from the analyzing diode, reflected by or transmitted through the analysis disc and read by the first photodetector.

According to the third aspect of the present invention, the optical analyzer according to the first aspect is provided, wherein the analyzing diode includes a plurality of analyzing diodes which emit laser beams having different wavelengths, and a final result of analysis of a same sample is provided based on a result of analysis of light emitted from one of the plurality of analyzing diodes, reflected by or transmitted through the analysis disc and read by the first photodetector, and on a result of light which is emitted from another analyzing diode among the plurality of analyzing diodes, reflected by or transmitted through the analysis disc and read by the first photodetector.

According to the fourth aspect of the present invention, there is provided an optical analyzer for optically analyzing a sample located on a part of an analysis disc while rotating the analysis disc, the analysis disc having a track on which address information is recorded, the optical analyzer including a reading diode emitting laser light for reading data concerning address information on the track of the analysis disc, an analyzing diode emitting to the sample laser light with a wavelength different from the wavelength of laser light emitted by the reading diode, and a photodetector for reading light emitted from the reading diode or the analyzing diode and reflected by the analysis disc, wherein position control of the reading diode and the analyzing diode in the direction of radius of the analysis disc is performed according to reading output from the photodetector, and a result of analysis of the sample is read from reading output from the photodetector, at a position on the analysis disc at which the sample is read.

According to the fifth aspect of the present invention, the optical analyzer according to the fourth aspect is provided, wherein a final result of analysis of a same sample is provided based on a result of analysis of light which is emitted from the reading diode and read by the photodetector at the position on the analysis disc at which the sample is read, and on a result of analysis of light which is emitted from the analyzing diode and read by the photodetector (PD2) at the position on the analysis disc at which the sample is read.

According to the sixth aspect of the present invention, the optical analyzer according to the first or fourth aspect is provided, wherein the analyzing diode includes a plurality of analyzing diodes which emit laser beams having different wavelengths.

According to the seventh aspect of the present invention, the optical analyzer according to the first or fourth aspect is provided, wherein the analyzing diode includes a plurality of analyzing diodes which emit laser beams having different wavelengths, and a final result of analysis of a same sample is provided based on a result of analysis of light which is emitted from one of the plurality of analyzing diodes and read by the photodetector at the position on the analysis disc at which the sample is read, and on a result of analysis of light which is emitted from another analyzing diode among the plurality of analyzing diodes and read by the photodetector at the position on the analysis disc at which the sample is read.

According to the eighth aspect of the present invention, the optical analyzer according to the first or fourth aspect is provided, wherein the reading diode and the analyzing diode are provided in a single pick-up.

According to the ninth aspect of the present invention, the optical analyzer according to the sixth aspect is provided, wherein if a plurality of samples are located in different positions in the direction of circumference of the analysis disc, the analyzing diodes are alternately selected and driven according to the positions of the samples.

According to the tenth aspect of the present invention, the optical analyzer according to the fourth aspect is provided, wherein the analyzing diodes are alternately selected and driven while the same sample is being scanned.

According to the eleventh aspect of the present invention, the optical analyzer according to the sixth aspect is provided, wherein the analyzing diodes are alternately selected and driven every predetermined number of rotations of the analysis disc.

According to the twelfth aspect of the present invention, the optical analyzer according to the first or fourth aspect is provided, wherein switching between output from the reading diode and output from the analyzing diodes is made by reading a marker provided on the analysis disc.

According to the thirtieth aspect of the present invention, the optical analyzer according to the first or fourth aspect includes a reading laser output driving unit driving the reading diode, an analyzing laser output driving unit driving the analyzing diode, a laser switching unit for switching output of the reading diode and the analyzing laser, a reading laser output monitoring unit monitoring laser emission from the reading diode, an analyzing laser output monitoring unit monitoring laser emission from the analyzing diode, and a laser output response measuring unit measuring, from output of each of the output monitoring units, a response time that elapses between a time point at which the reading laser output driving unit or the analyzing laser output driving unit starts driving and a time point at which a predetermined level of laser is emitted, wherein when switching between the reading diode laser emission and the analyzing diode laser emission is made, the laser output response measuring unit causes each laser output driving unit to start driving the next reading diode or analyzing diode to emit laser light in advance of an emission start time for the next reading diode or the or the analyzing diode by an amount of time equal to or close to the response time.

According to the fortieth aspect of the present invention, the optical analyzer according to the thirtieth aspect is provided, wherein the response time of a diode used for analysis is measured when the reading laser or the analyzing laser is driven.

According to the fiftieth aspect of the present invention, the optical analyzer according to the thirtieth aspect is provided, wherein the reading laser output driving unit and the analyzing laser output driving unit apply a bias current to their corresponding diodes even while the diodes are not emitting laser.

According to the sixtieth aspect of the present invention, the optical analyzer according to the second or fifth aspect is provided, wherein in a section where an analyzing diode emits laser light, the optical pick-up is held at a position at which the reading diode emitted laser for the last time.

According to the seventieth aspect of the present invention, the optical analyzer according to the first or fourth aspect is provided, wherein the reading diode is used to obtain image data of the sample and the analyzing diode is used to obtain calorimetric data on the sample.

According to the eightieth aspect of the present invention, the optical analyzer according to the third or seventh aspect is provided, wherein the wavelengths of laser light of the analyzing diodes are alternately selected every predetermined number of rotations of the analysis disc, or laser outputs of the plurality of analyzing diodes are alternately selected during a predetermined rotation of the analysis disc.

With the optical analyzer of the present invention, information represented by pits or wobble grooves on a disc can be obtained and different laser wavelengths suitable for analyzing different samples can be used.

Furthermore, because a number of lasers with different wavelengths are provided and switching between them is performed quickly in the optical analyzer of the present invention, contiguous scanning of a disc can be performed even if more than one laser is required for scanning multiple samples having different optical characteristics on the single disc.

BRIEF DESCRIPTION OF THE DRAWINGS

FIG. 2 is a top view of an analysis disc used in the first embodiment;

FIG. 3 is across-sectional view of the analysis disc used in the first embodiment;

DESCRIPTION OF THE EMBODIMENTS

Embodiments of an optical analyzer of the present invention will be described below.

First Embodiment

FIGS. 1 to 5 show an optical analyzer according to the present invention.

Figure 1:
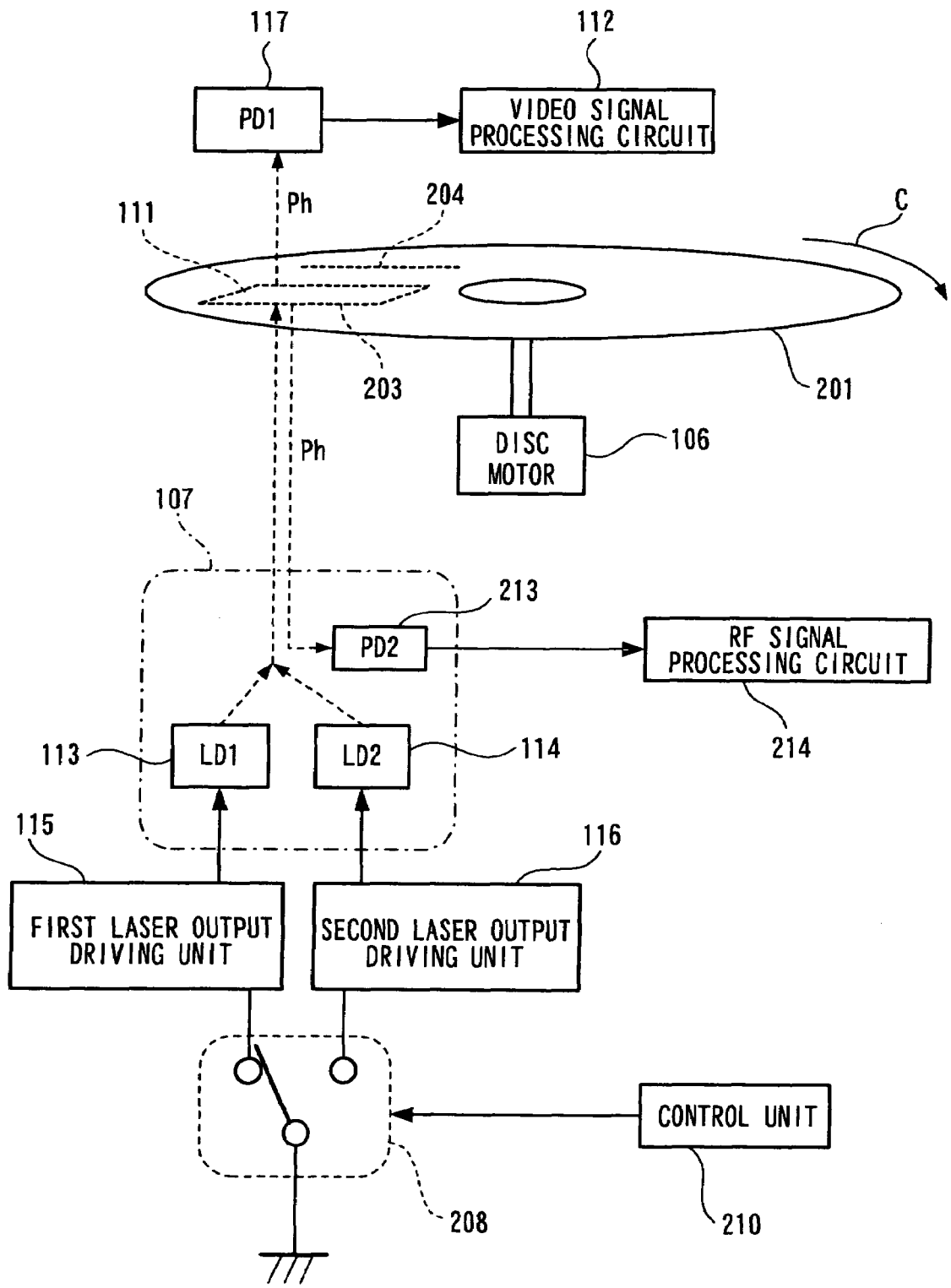
FIG. 1 is a block diagram showing a configuration of an optical analyzer according to a first embodiment of the present invention.
Figure 10:
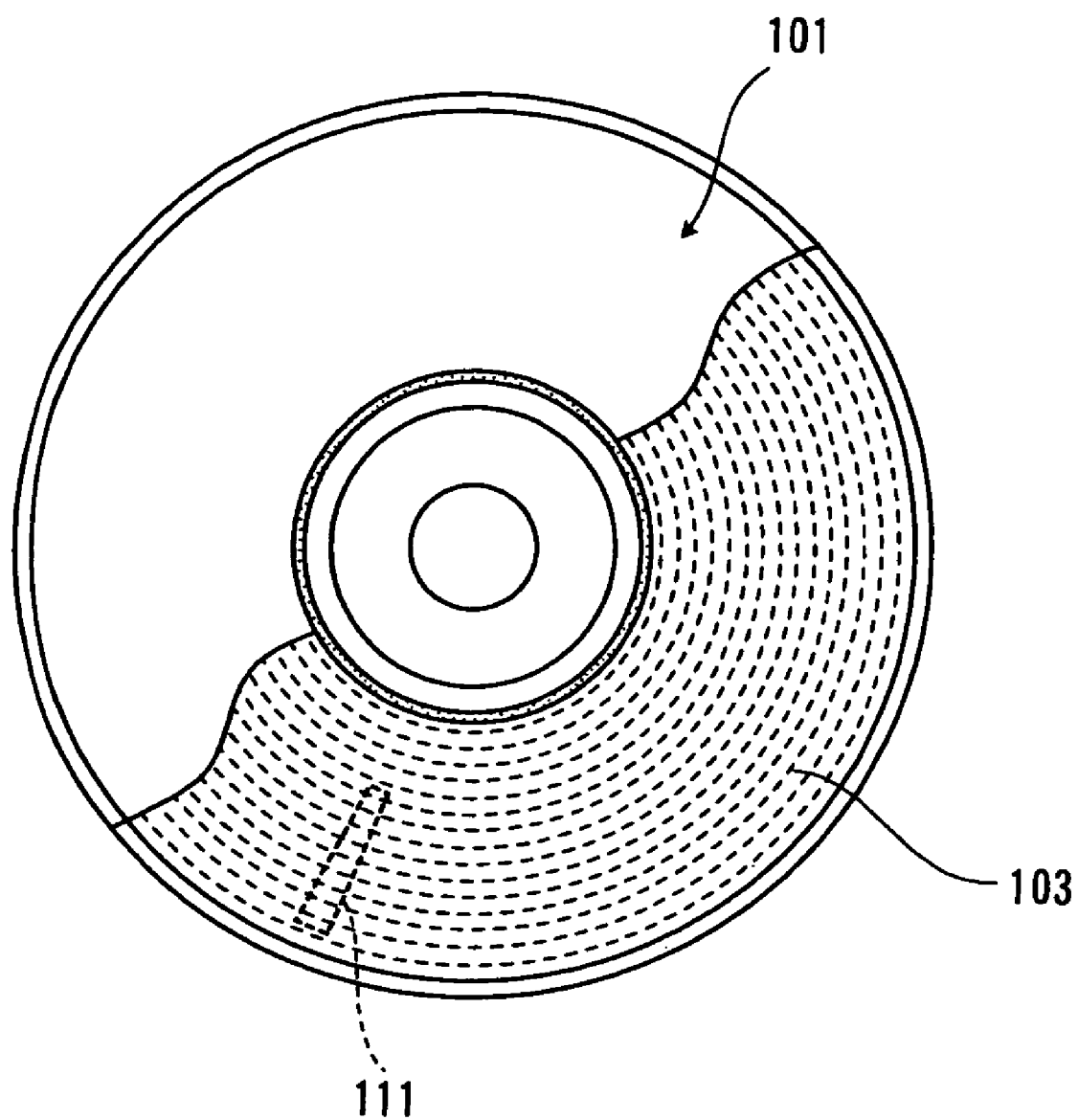
FIG. 10 is a cutaway top view of a conventional analysis disc.
Figure 11:
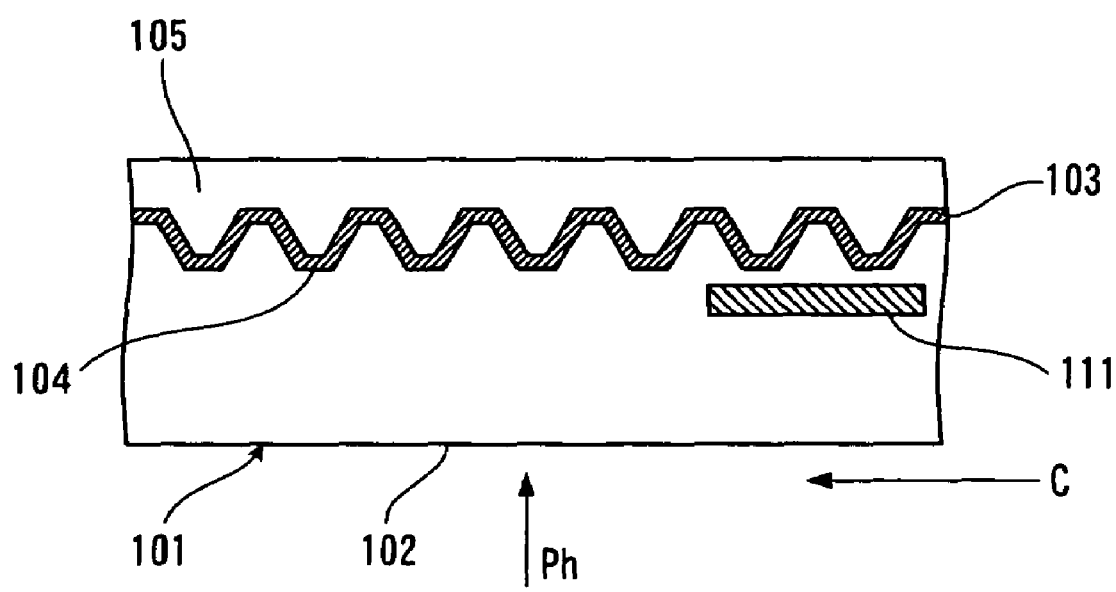
FIG. 11 is a cross-sectional view of the conventional analysis disc.

FIG. 1 shows an optical analyzer according to a first embodiment of the present invention. Provided on an analysis disc 201 are concentric tracks shown in FIG. 10 or a spiral track (not shown) and a region in which a biological, chemical, or biochemical sample 111 is provided. A pick-up 107 which accesses the analysis disc 201 includes a first laser diode (LD1) 113 that emits laser light with a wavelength suitable for reading information existing as pits or wobble grooves on the track(s) of the analysis disc 201 and a second laser diode (LD2) 114 that emits laser light with a wavelength suitable for analyzing optical properties of the sample 111.

Components of the laser beams emitted from the first and second laser diodes 113, 114 that pass through the analysis disc 201 are detected at a first photodetector (PD1) 117 and then sent to a video signal processing circuit 112. Components reflected by the analysis disc 201 are detected at a second photodetector (PD2) 213 provided in the same pick-up 107 and then sent to an RF signal processing circuit 214.

The first photodetector (PD1) 117 may be a line sensor which extends and is fixed along the radius of the analysis disc 201 or may be a sensor which does not extend along the radius of the analysis disc 201 like the second photodetector (PD2) 213 and which is moved in the direction of the radius of the analysis disc 201 in the same way as the pick-up 107 is moved.

The first laser diode 113 is driven by a first laser output driving unit 115 and the second laser diode 114 is driven by a second laser output driving unit 116. On of the first and second laser output driving unit 115, 116 is selected to work by a selector switch 208 under the control of a microcomputer-based control unit 210.

The analysis disc 201, which is rotated by a disc motor 106, rotates in the direction indicated by arrow C. A marker 204 is provided in a position scanned by the laser before the sample 111 on the analysis disc 201.

The sample 111 provided on the analysis disc 201 as shown in FIG. 2 is a mixture of the sample and a reagent chosen according to characteristics to be analyzed. The marker 204 is recorded only in a position immediately before, in the rotation direction C, the read area 203 in which the sample 111 is provided across the read area in the direction of the radius (the direction indicated by arrow A). More specifically, the sample 111 on the analysis disc 201 is provided between the surface 202a of the analysis disc 201 and the track 103, as shown in FIG. 3. The marker 204 is printed in ink as a strip on the back surface 202b of the analysis disc 202. Reference numeral 206 in FIG. 3 indicates a pit or wobble formed in the mirror-finished track 103. Reference numeral 207 indicates a land formed in the mirror-finished track 103.

It should be noted that the above description also applies to a case where the sample 111 is provided between the back surface 202b of the analysis disc 201 and the track 103 as shown by a phantom line in FIG. 3.

Referring to FIG. 1, a laser beam emitted from the firs laser diode (LD1) 113 or the second laser diode (LD2) 114 is applied to the analysis disc 201, and data signals represented by pits or wobbled on the analysis disc 201 are reflected from lands 207 on the analysis disc 201, read by the second photodetector (PD2) 213 in the pick-up 107, and processed at the RF signal processing circuit 214.

The lands 207 on the analysis disc 201 are formed by vapor deposition of a thin layer of a metal such gold so that a reflectivity in the range from between 30 and 60% of the lands 207 can be achieved. Part of the laser light also passes through the analysis disc 201 and reaches the first photodetector (PD1) 117 above the analysis disc 201. The laser light also passes through the sample 111 on the analysis disc 201 and the pattern of light and shade of the sample 111 are read by the first photodetector (PD1) 117 and signals representing the pattern are processed in the video signal processing circuit 112.

When the region of the analysis disc 201 where the sample 111 is not provided is over the pick-up 107, the control unit 210 switches the selector switch 208 to cause the first laser output driving unit 115 to drive the first laser diode (LD1) 113 to emit laser light. When the control unit 210 detects the marker 204, the control unit 210 switches the selector switch 208 to cause the second laser diode (LD2) 114 to emit laser light.

The optical pick-up 107 may be a single pick-up in which lasers designed for CD (Compact Disc)/DVD (Digital Versatile Disc) is provided. Alternatively, the optical pickup 107 may be one on which a laser diode for DVD/"Blu-ray Disc" and a laser diode for CD/DVD/"Blu-ray Disc" are provided.

If an analysis disc 201 on which a track in CD format is formed is scanned, a laser with a wavelength, for example 780 nm, suitable for obtaining data represented by pits or wobble grooves on the disc is used as the first laser diode (LD1) 113 and a laser with a wavelength of 650 nm, which helps to obtain a light and shade response of a sample 111 is used as the second laser diode (LD2) 114.

Figure 4:
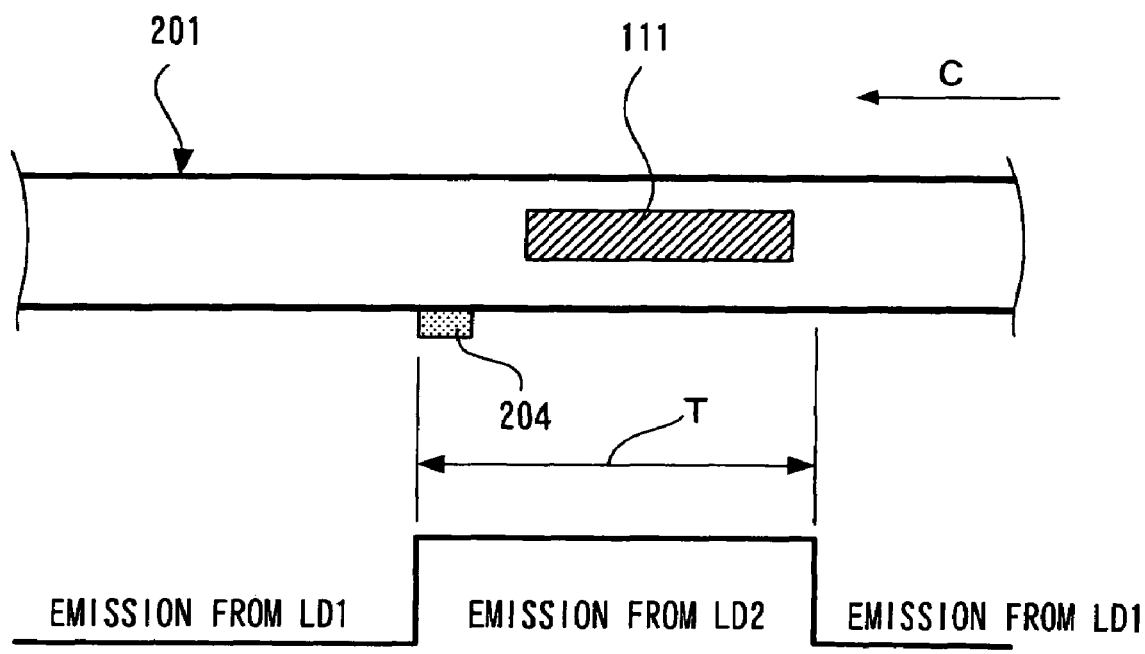
FIG. 4 is a laser switching timing chart.

FIG. 4 shows an example of timing of switching of the selector switch 208 by the control unit 210. As shown in FIG. 4, the control unit 210 switches the selector switch 208 for a predetermined period of time T required for tracing the sample 111 region from the time when it detects the marker 204 during tracking by the first laser diode (LD1) 113 to cause the second laser diode (LD2) 114 to emit laser light.

Figure 5:
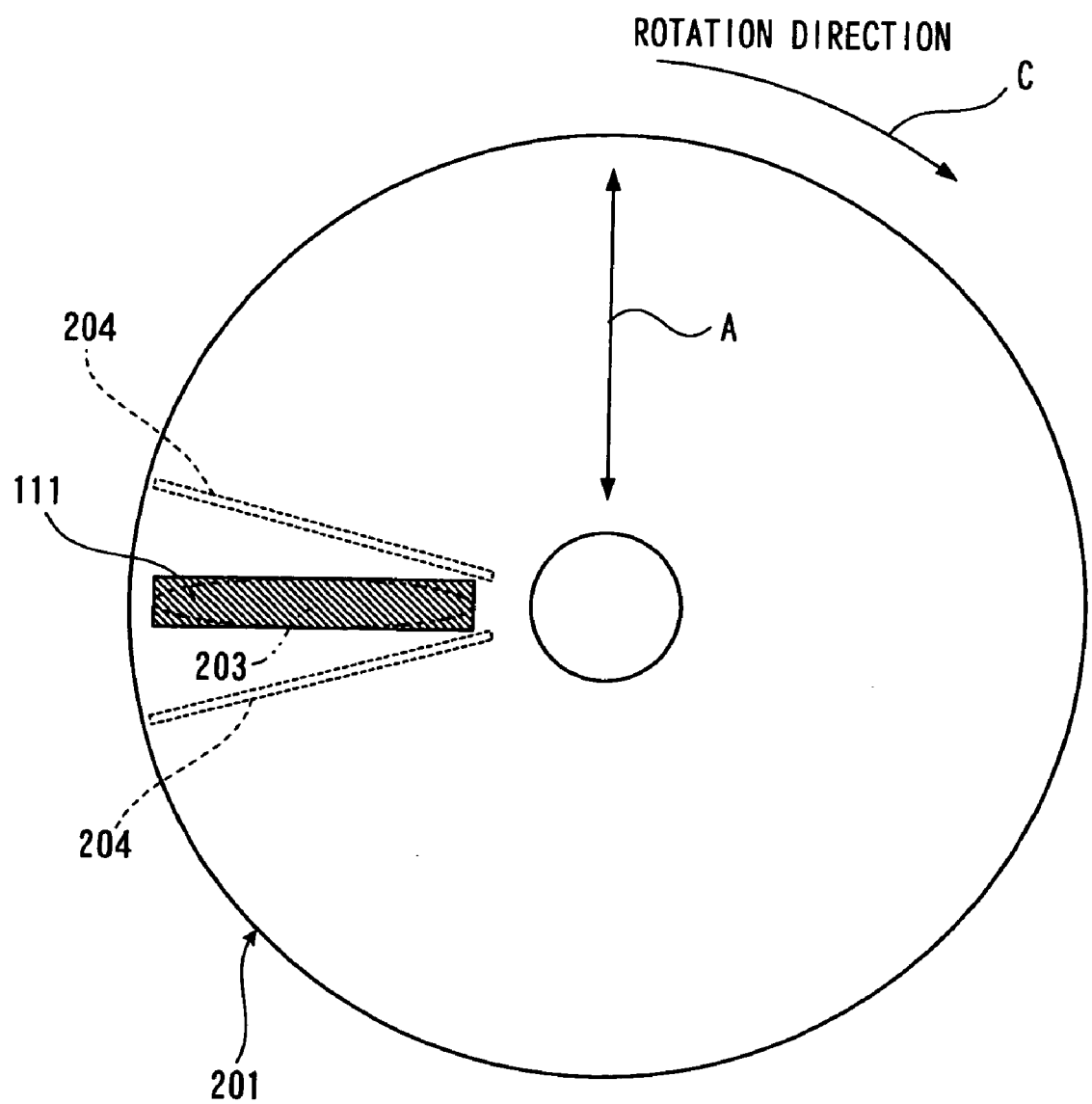
FIG. 5 is a top view of an analysis disc having marks around a sample.
Figure 12:
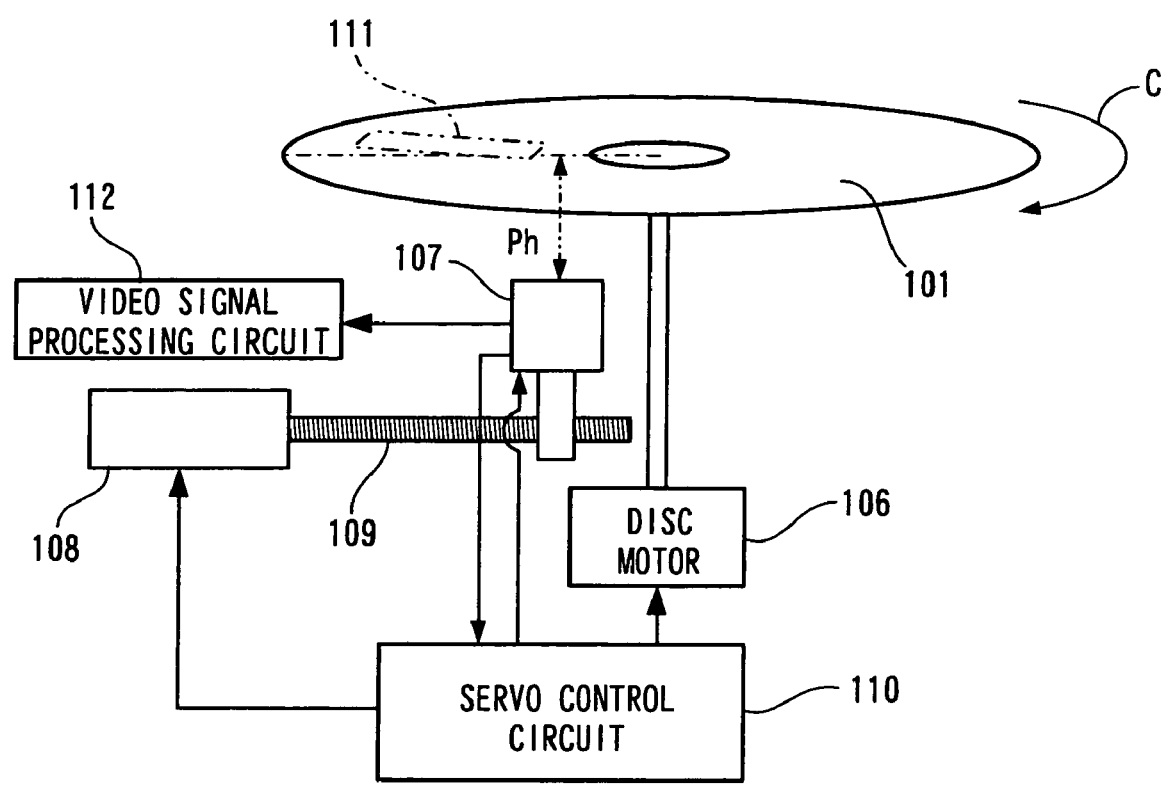
FIG. 12 is a block diagram of a typical optical disc drive unit.

If the marker 204 is provided to the rear of the sample 111 in addition to the marker 204 ahead of the sample as shown in FIG. 5, the rear marker 204 can be used to end the period during which scanning is performed by emission from the second laser diode (LD2) 114 and return to the scanning by the emission from the first laser diode (LD1) 113, without having to preset the time T. Because servo signals such as tracking signals cannot be obtained during the period in which the second laser diode (LD2) 114 is emitting light if the additional marker 204 is provided to the rear of the sample 111, a track-tracking control unit consisting of a servo control circuit 110, a traverse motor 108, and a lead screw 109 as shown in FIG. 12 is used to hold the pick-up 107 just as in the case of tracing a defective disc, thereby allowing the tracking of the surface and track of the analysis disc 201 to be kept at the last position at which the first laser diode (LD1) 113 emitted light (the position at which the pick-up 107 was positioned immediately before the switching to the second laser diode (LD2) 114). This configuration prevents the position of the pick-up 107 from substantially changing and ensures more accurate analysis after switching to emission from the second laser diode (LD2) 114.

According to the first embodiment, a diode for conducting analysis is provided separately from a diode for reading data, as has been described above. Therefore, a diode emitting laser light with a wavelength suitable for reading data from bits and wobble grooves on an analysis disc 201 can be chosen as the first laser diode (LD1) 113. For example, for reading bits or wobble grooves based on CD standards, a diode emitting laser light with a wavelength of around 780 nm may be chosen; for reading data from bits or wobble grooves specified in DVD standards, a diode emitting laser light with a wavelength of around 650 nm may be chosen; and for reading data from bits or wobble grooves based on the Blu-ray Disc standard, a diode emitting light with a wavelength of 405 nm maybe chosen. Laser of any wavelength may be chosen without regard data to be read. If the optical analyzer of the present invention is used for quantification of chemical species in a solution using the absorbance, optical characteristics (absorption spectrum) of the substance to be measured is measured beforehand and a second laser diode (LD2) 114 that emits laser light with a wavelength close to the wavelength best suited to the measurement can be chosen.

For typical quantification of chemical species in a solution using absorbance, any wavelength may be chosen in principle that allows light absorption. However, a wavelength that does not cause substantial fluctuation of absorbance, that is, the maximum absorbance wavelength, is often most suitable for measurement of absorbance because light can be detected by integrating the intensities of light of wavelengths in a finite range. When analysis of multiple types of samples (analysis of samples having multiple optical characteristics) is performed by using a single analyzer or a single analysis disc, it is a very advantageous that the single device can output and analyze a number of wavelengths.

Furthermore, if optical characteristics of samples 111 is to be obtained as image data, it is preferably that analysis is performed with a laser of as short a wavelength as possible and as small a scan track pitch as possible to obtain more detailed image data. However, for analysis using absorbance, a shorter wavelength is not always preferable because optimum wavelengths vary from sample 111 to sample 111 as mentioned earlier. The present invention is very advantageous when these two types of analysis are to be performed with a single analyzer or a single analysis discs.

If a sample is analyzed by using an analysis disc on which bits or wobble grooves based on the Blu-ray standard are provided in the regions other than the analysis region, a finer image than an image obtained by analysis using an analytical disk having bits or wobble grooves based on CD or DVD standards can be obtained by using a laser of a wavelength of 405 nm for the sample 111 and using a track pitch of 0.32 µm. This is because the fineness of image analysis of a sample 111 on an analysis disc 201 largely depends on the track pitch scanned and the wavelength used and can be improved by using a wavelength as short as possible and a scan track pitch as small as possible.

By using a pick-up 107 containing diodes emitting light of different wavelengths for CD and DVD, the range of wavelengths that can be used for absorbance-based analysis can be widened up to 650 nm and 780 m. Accordingly, more suitable wavelengths can be used according to optical characteristic of samples.

When the absorbance of a soluble formazan commonly called WST-4 (manufactured by DOJINDO laboratories), which is generated from a tetrazolium salt by reduction with NADH, is measured, analysis with a laser of a DVD wavelength is advantageous because the dependency of absorbance on the concentration appear around 650 nm, which is a DVD standard value but the dependency on concentration is low at wavelengths around a Blu-ray-disc-standard wavelength of 405 nm or a CD-standard wavelength of 780 nm.

The absorbance of a soluble formazan commonly called WST-3 (manufactured by DOJINDO laboratories), which is generated from a tetrazolium salt by reduction with NADH, is maximized at a wavelength of 433 nm. In this case, almost no light is absorbed at wavelengths longer than approximately 600 nm. Therefore, a more accurate analysis can be accomplished by using a laser of a wavelength of 405 nm based on the Blu-ray Disc standard at which a high concentration-dependency appears.

It is advantageous that more than one wavelength can be used to perform absorbance analysis of a wide variety of substances having different absorption spectra, because an extended range of substances can be analyzed by using a single analyzer with an improved accuracy.

Second Embodiment

Figure 6:
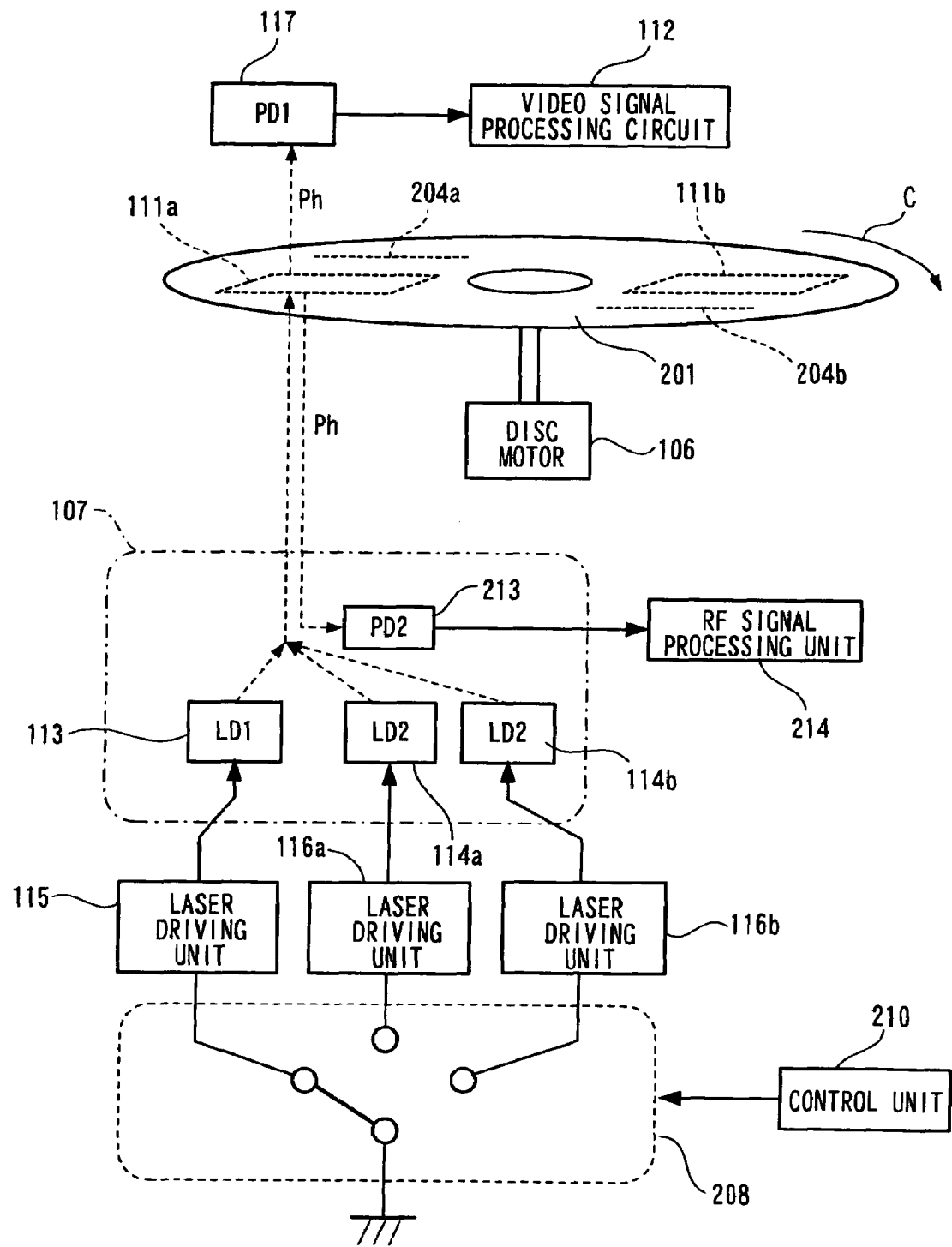
FIG. 6 is a block diagram showing a configuration of an optical analyzer according to a second embodiment of the present invention.
Figure 7:
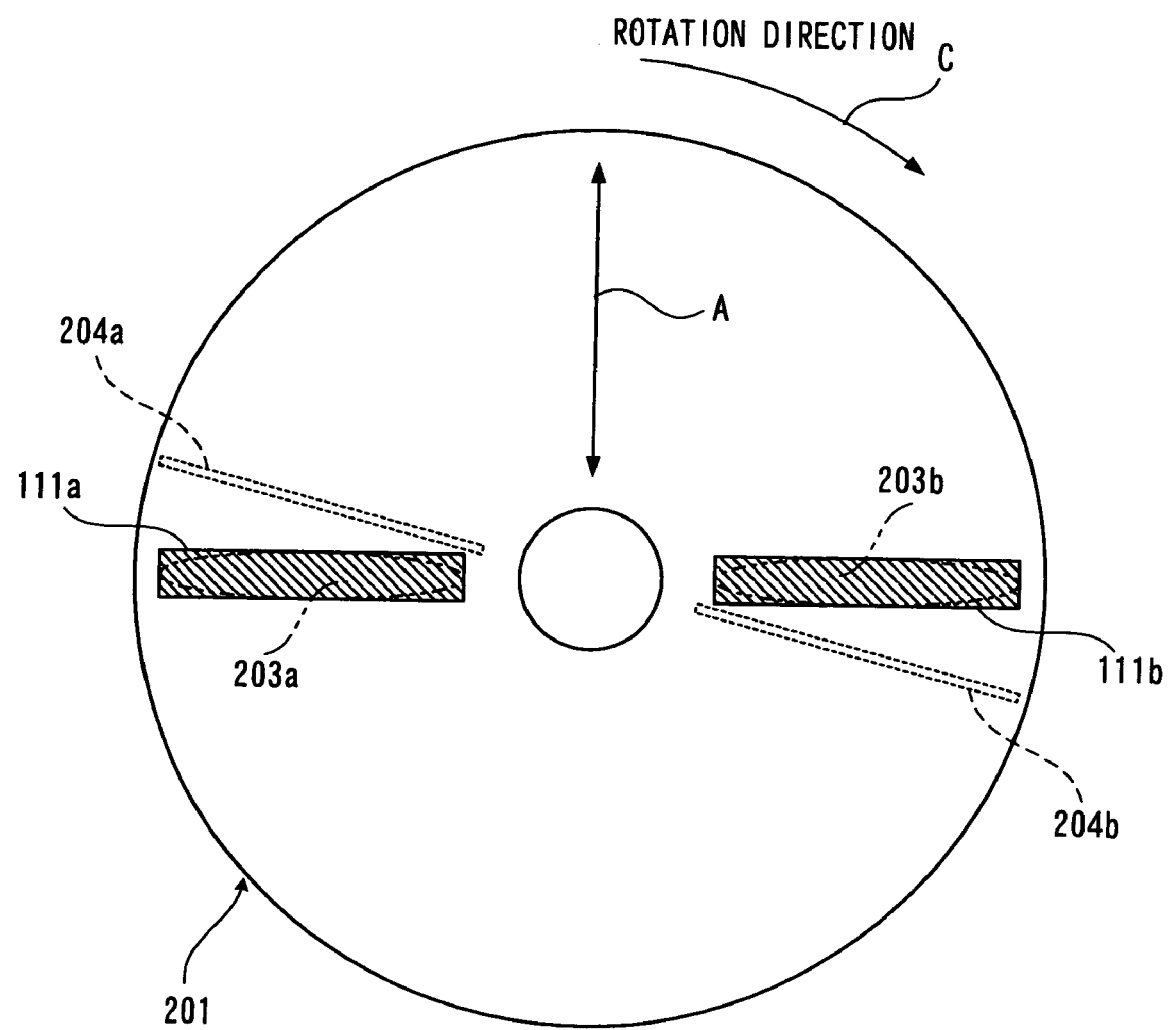
FIG. 7 is a plan view of an analysis disc used in the second embodiment.

FIGS. 6 and 7 show an optical analyzer according to a second embodiment of the present invention.

In the first embodiment, a first laser diode (LD1) 113 and a second laser diode (LD2) 114 are provided, the first laser diode (LD1) 113 is used for obtaining data represented by pits or wobble grooves on a disc and the second laser diode (LD2) 114 is used for obtaining a light and shade response of a sample 111. The second embodiment provides an optical analyzer which woks on an analysis disc 201 having concentric tracks or a spiral track (not shown) and multiple regions in which biological, chemical, or biochemical samples 111*a*, 111*b* are provided.

In particular, a single pick-up 107 shown in FIG. 6 includes a first laser diode (LD1) 113 that emits laser light with a wavelength suitable for reading information represented by pits and wobble grooves on the track of an analysis disc 210, a second laser diode (LD2) 114a that emits laser light with a wavelength suitable for analyzing optical characteristics of a sample 111a, and a third laser diode (LD3) 114b that emits laser light with a wavelength suitable for analyzing another sample 111b.

Components of the laser light outputted from the pick-up 107 that pass through the analysis disc 201 are detected at a first photodetector (PD1) 117 and their signals are processed by video signal processing circuit 112. Components reflected off the analysis disc 201 are detected at a second photodetector (PD2) 213 and then sent to an RF signal processing circuit 214.

The first laser diode (LD1) 113 is driven by a first laser driving unit 115, the second laser diode (LD2) 114a is driven by a second laser driving unit 116a, and the third laser diode (LD3) 114b is driven by a third laser driving unit 116b. A control unit 210 switches the first to third laser driving unit 115, 116a, 116b through a selector switch 208.

A disc motor 106 drives the analysis disc 201 in the direction indicated by arrow c. Samples 111a, 111b are provided in a number of positions (two positions in this example) on the analysis disc 201 as shown in FIG. 7 and markers 204a, 204b are provided in positions which are scanned by the lasers before the samples 111a, 111b.

The samples 111a and 111b are mixtures of samples and reagents suitable chosen according to characteristics to be inspected. The markers 204a and 204b are recorded in positions immediately before the read area 203a and 203b in which the samples 111a and 111b are provided in the rotation direction C across the read areas in the direction of the radius (direction indicated by arrow A).

A position of the selector switch 208 is selected by the control unit 210, laser light is emitted from the first laser diode (LD1) 113 and reflected off lands 207 on the analysis disc 210, and signals from bits or wobble grooves on the analysis disc 210 are detected by the second photodetector (PD2) 213 in the pick-up 107 and processed in the RF signal processing circuit 214.

A thin reflective film (not shown) of the analysis disk 201 is formed of a metal such as gold by vapor deposition so that a reflectivity in the range from 30 to 60% is provided. Part of laser light passes through the disc 201 and reaches the PD1 (117) provided above the disc 201. Light also passes through the samples 111a and 111b on the analysis disc 201. Consequently, optical effects of the samples are reflected in output signals of the first photodetector (PD1) 117. These signals are processed in the video signal processing circuit 112.

As has been described with respect to the first embodiment, in typical quantification of chemical species in a solution, different samples to be analyzed using absorbance often have different absorption spectra and therefore different optimum wavelengths are used for different types. The arrangement that allows one of multiple types of analyzing lasers is useful in measuring each of different types of samples under optimum conditions.

In this way, according to the present invention, a number of diodes for analysis are provided in an analyzer so that a wavelength suitable for each of various samples can be selected. Therefore, an extended range of samples can be analyzed by using the single analyzer.

If different types of samples are located in sample regions 111a and 111b, one of the analyzing diodes 114a and 114b that is suitable for each of them can be selected and used. Therefore, the samples to be analyzed can be analyzed by using different wavelengths suitable for them during one rotation.

Furthermore, while one sample 111a or 111b is being scanned, switching can be made from the second laser diode (LD2) 114a to the third laser diode (LD3) 114b to cause it emit laser.

In a basic configuration of the present invention, a sample on a rotating analysis disc 201 is scanned by using laser light emitted from a fixed diode. One of the analyzing diodes emitting laser light of different wavelengths can be selected and used for the same analysis region on a rotation-by-rotation basis. Because the regions other than the sample regions 111a and 111b on the disc can be tracked accurately by the pick-up 107 using laser light emitted from the first laser diode (LD1) 113, a regions tracked by the second laser diode (LD2) 114a can be accurately re-scanned by the third laser diode (LD3) 114b, for example. Analytical data obtained on one sample 111a or 111b by using more than one wavelength in this way is useful for canceling the influence of turbidity of the sample to be analyzed.

In the present embodiment, the control unit 210 is configured so that after the second laser diode (LD2) 114a with a wavelength close to a maximum absorption wavelength specific to a sample 111a or 111b scans the sample 111a or 111b, the third laser diode (LD3) 114b with a wavelength far from the maximum absorption wavelength specific to the sample 111a or 111b scans the region in which the same sample 111a or 111b is present, and the video signal processing circuit 112 is configured so as to calculate the difference between the absorbances obtained. This allows the influence of turbidity of the sample to be canceled.

In that case, the control unit 210 may switch between the second laser diode (LD2) 114a and the third laser diode (LD3) 114b while the sample 111a or 111b is being scanned, so that data can be obtained in a region or regions in which the same sample exists by using the second laser diode (LD2) 114a and the third laser diode (LD3) 114b during one rotation.

Furthermore, the control unit 210 is configured to switch between the second laser diode (LD2) 114a and the third laser diode (LD3) 114b every one rotation or a predetermined number of rotations of the analysis disc 201 or every time the disc rotates by a predetermined angle, to obtain different signals at the same position.

This can be accomplished because the pick-up 107 can keep tracking accurately in the regions where no sample exist on the analysis disc 201 with laser light emitted from the firs laser diode (LD1) 113 and thereby laser light emitted from the second laser diode (LD2) 114a and the third laser diode (LD3) 114b can be accurately focused on a targeted position in every rotation.

While the second laser diode (LD2) 114a and the third laser diode (LD3) 114b are emitting light, the pick-up 107 can be held from tracking to enable the third laser diode (LD3) 114b to more accurately scan the regions scanned by the second laser diode (LD2) 114a, for example.

Furthermore, different kinds of analysis data on a single sample can be obtained by using the second laser diode (LD2) 114a and the third laser diode (LD3) 114b. This is useful when two substances having different optical characteristics are located in one sample regions and both of them are to be analyzed because a wavelength suitable for each of the substances can be selected to obtain data on the substances at a time. This configuration is also effective in avoiding the influence of an interfering substance in the sample. When more than one laser is used to scan one sample region, a wavelength suitable for the substance to be analyzed and another wavelength for the interfering substance can be used to scan the substances to measure their absorbances and the measured absorbances can be used to cancel the influence of the interfering substance.

If this configuration is used for obtaining the ratio between oxygenated hemoglobin and deoxidized hemoglobin in a mixture, for example, the ratio can be known by measuring the absorbance of the same sample at a wavelength of 805 nm at which they exhibit an identical absorbance (isosbestic point) and a wavelength greater than this, for example, a wavelength in the range between around 640 and 660 nm.

While the present embodiment has been described with respect to examples in which two analyzing lasers are provided and switching is made between them, one of the two analyzing lasers may also be used as a reading laser, as described earlier. The present invention is also effective in the case where three or more analyzing lasers, which may be laser diodes used for recording/playback of CD, DVD, or Blue-ray disc, are provided and one of which is selected to be used in analysis.

Third Embodiment

Figure 8:
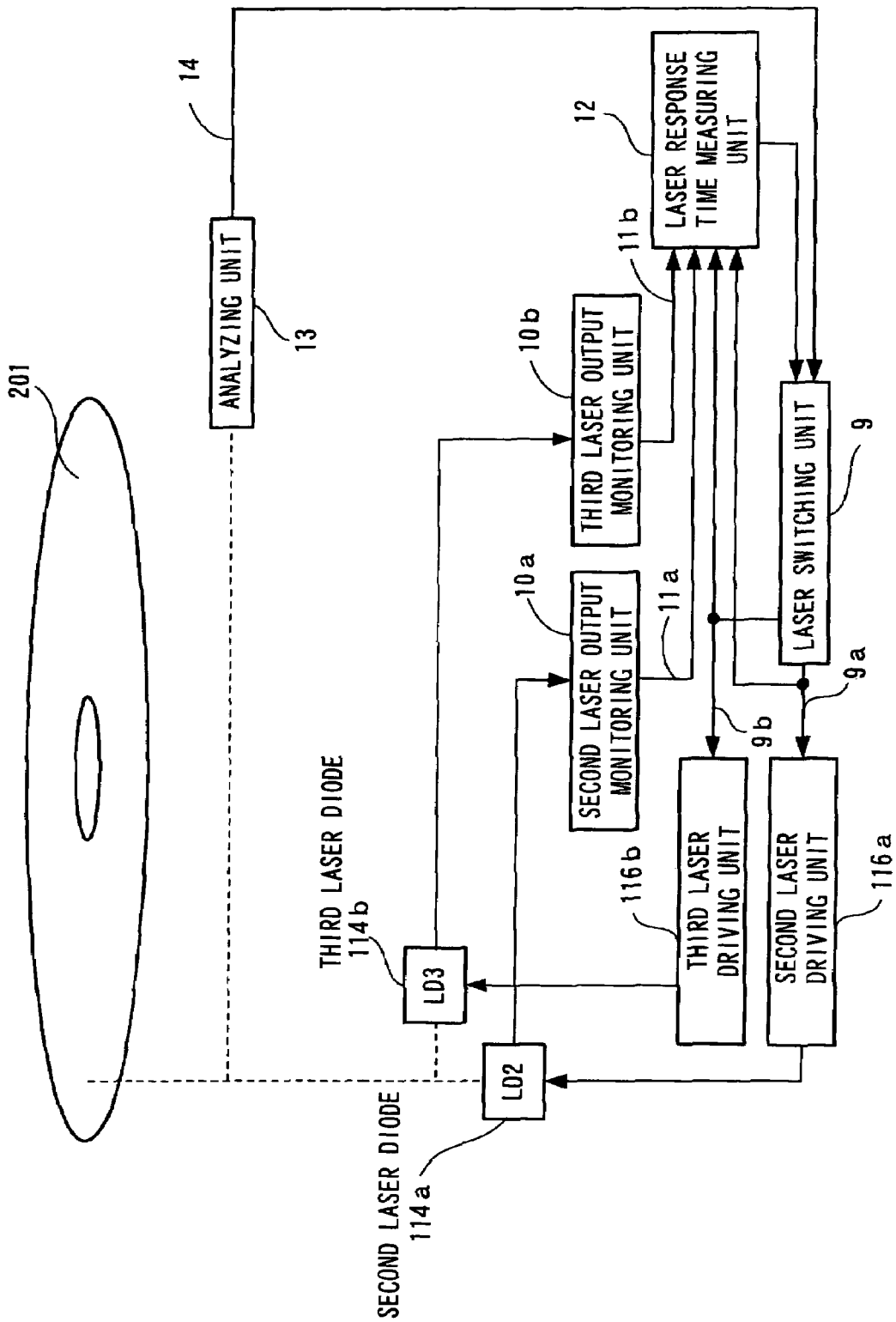
FIG. 8 is a block diagram of a laser switching unit and driving units of an optical analyzer according to a third embodiment of the present invention.

FIG. 8 shows a specific example of the laser switching unit and laser driving units, and control unit 210 of the second laser diode (LD2) 114a and third laser diode (LD3) 114b shown in FIG. 6. FIGS. 9A to 9E show timing chart of signals in the example shown in FIG. 8. The laser switching unit 9 in FIG. 8 outputs a second laser driving signal 9a shown in FIG. 9B or a third laser driving signal 9b shown in 9D.

The second laser output driving unit 116a uses the second laser driving signal 9a to drive the second laser diode (LD2) 114a and the third laser output driving unit 116b uses the third laser driving signal 9b to drive the third laser diode (LD3) 114b.

Laser output of the second laser output driving unit 116a which is monitored by a second laser output monitoring unit 10a outputs a second laser output monitoring signal 11a. Laser output of the third laser output driving unit 116b which is monitored by a third laser output monitoring unit 10b outputs a third laser output monitoring signal 11b.

Figure 9:
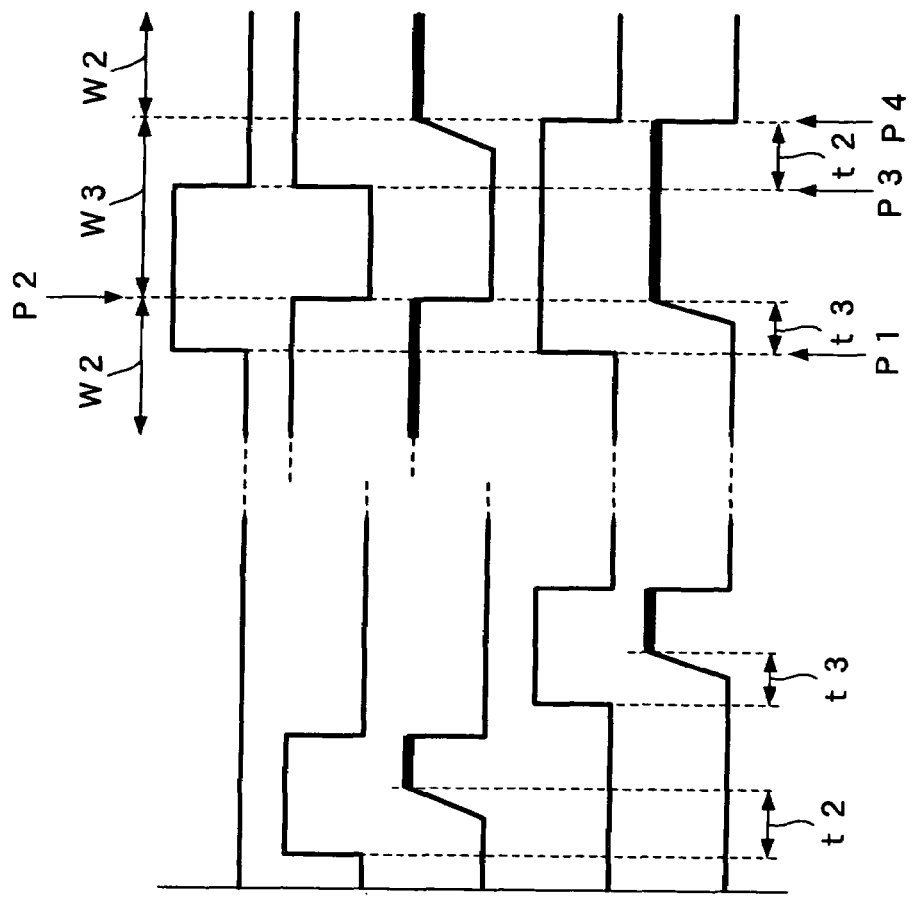
FIGS. 9A to 9E are timing charts showing operations according to the third embodiment.

A laser response time measuring unit 12 uses the second laser driving unit 9a and the second laser output monitoring signal 11a shown in FIG. 9C to measure the response time t2 that elapses before the second laser diode (LD2) 114a emits laser light. It also uses the third laser driving signal 9b and the third laser output monitoring signal 11b shown in FIG. 9E to measure the response time t3 that elapses before the third laser diode (LD3) 114b emits laser light, and stores the response times t2 and t3.

An analyzing unit 13 outputs an analysis trigger signal 14 shown in FIG. 9A at predetermining timing. In response to the analysis trigger signal 14, the laser switching unit 9 starts a laser switching operation. The output of the analysis trigger signal 14 may also be outputted when scanning laser light passes through a marker 204, in addition to the predetermined timing.

If laser light is emitted from the second laser diode (LD2) 114a at the rising edge P1 of the analysis trigger signal 14 as shown in FIGS. 9A and 9B, the third laser driving signal 9b is issued as shown in FIGS. 9C and 9D and a switching operation is started in order to cause the third laser diode (LD3) 114b to emit laser light. Because the response time t3 of the third laser diode (LD3) 114b obtained previously has been stored, the time that will expire between the output of the third laser driving signal 9b and the peak of the laser emission from the third laser diode (LD3) 114b can be known. By delaying termination of output of laser light from the second laser diode (LD2) 114a for a time equal to the stored response time t3 with respect to the timing P1 generating the third laser driving signal 9b, the peak of laser light output from the third laser diode (LD3) 114b can be brought into coincidence with the timing P2 at which laser light output from the second laser diode (LD2) 114 ceases. Consequently, analysis can be performed without a break between the analysis period W2 during which the wavelength of laser light from the second laser diode (LD2) 114a is being used and the analysis period W3 during which the wavelength of laser light from the third laser diode (LD3) 114b is being used.

Similarly, switching from emission from the third laser diode (LD3) 114b to emission from the second laser diode (LD2) 114a can be seamlessly made. In the present embodiment, the second laser driving signal 9a is outputted at rising edge P3 of the analysis trigger signal 14. Because the previously obtained response time t2 of the second laser diode (LD2) 114a is stored, the time that will elapse between the output of the second laser driving signal 9a and the peak of the laser emission from the laser diode (LD2) 114a can be known. By delaying the laser light emission from the third laser diode (LD3) 114b for a time equal to the stored response time t2 with respect to the timing P3 generating the second laser driving signal 9a, the peak of laser emission from the second laser diode (LD2) 114a can be brought into coincidence with the timing P4 at which the laser emission from the third laser diode (LD3) 114b ceases. Consequently, analysis can be performed without a break between the analysis period W3 during which the wavelength of laser light from the third laser diode (LD3) 114b is being used and the analysis period W2 during which the wavelength of laser light from the second laser diode (LD2) 114a is being used.

The analysis disc 201 includes a region or regions where a sample is located and other regions. Switching between multiple lasers can be efficiently made in a sample region, the area of which is limited.

While the response times t2 and t3 are measured and updated each time the second laser diode (LD2) 114a and the third laser diode (LD3) 114b are driven in the example described above, the response times of the second laser diode (LD2) 114a and the third laser diode (LD3) 114b may be measured and stored beforehand and an setting operation may be performed to select one of them in driving to bring the peak of laser emission from the next driven laser diode at the timing at which laser emission from the previous diode ceases.

A diode that is not being driven to emit laser light (in waiting state) may be kept supplied with a bias current so that the response time of the laser diode in waiting state can be effectively reduced. Preferably, the bias current should be less than a threshold current over which the diode start to emit laser light and greater than or equal to 80% the threshold current. If a diode designed for CD is used as the second laser diode (LD2) 114a, the diode is kept supplied with a bias current of 25 mA, with respect to the threshold current of 30 mA required for laser emission. If a diode designed for DVD is used as the third laser diode (LD3) 114b, the diode is kept supplied with a bias current of 20 mA, with respect to the threshold current of 25 mA required for laser emission. This can be reduce the response time compared with the case where no bias current is supplied.

While a form of switching between two diodes for analysis, the second laser diode (LD2) 114a and the third laser diode (LD3) 114b has been described in the above embodiments, a similar form can be used for switching among three or more analyzing diodes. Furthermore, a similar form can be used for switching between the first laser diode (LD1) 113, which is a diode for reading data, and a diode for analysis.

When switching between a reading laser and an analyzing laser or between analyzing lasers is made, the laser output driving unit starts driving the next diode to emit laser light an amount of time equal to the response time before the time at which the next diode should start emission. However, the laser output driving unit may start driving the diode to emit laser light an amount of time closer to the response time before the next analyzing diode or reading diode should start emission.

The first photodetector (PD1) 117 is disposed above the analytic disc 201 for detecting light which is emitted from the reading laser diode (LD1) 113 or the analyzing laser diodes (LD2, LD3) and passes through the analytic disc 201. However, the first photodetector (PD1) 117 may be disposed under the analysis disc 201, that is, on the pick-up 107 side, for detecting light which is emitted from the reading laser diode (LD1) 113 or the analyzing laser diodes (LD2, LD3) and reflected off the analysis disc 201. In that case, the first photodetector (PD1) 117 and the second photodetector (PD2) 213 may be separately provided or the second photodetector (PD2) 213 alone may be provided without providing the first photodetector (PD1) 117. In the latter case, signals are provided from the output of the second photodetector (PD2) 213 to the video signal processing circuit 112 and the RF signal processing circuit 214.

The optical analyzer according to the present invention can be used for analysis of optical characteristics of a wide variety of samples such as biological, chemical, or biochemical samples and is especially useful in medical analysis for measuring levels of fat and sugar in blood.

What is claimed is:

1. An optical analyzer for optically analyzing a sample located on a part of an analysis disc while rotating the analysis disc, the analysis disc having a track on which address information is recorded, the optical analyzer comprising:
   a reading diode emitting laser light for reading data concerning address information on the track of the analysis disc;
   an analyzing diode emitting to the sample laser light with a wavelength different from that of laser light emitted by the reading diode;
   a first photodetector for reading light emitted from the reading diode or the analyzing diode and reflected by or transmitted through the analysis disc; and
   a second photodetector for reading light emitted from the reading diode or the analyzing diode and reflected by the analysis disc, wherein
   position control of the reading diode and the analyzing diode in the direction of radius of the analysis disc is performed according to reading output from the second photodetector, and a result of analysis of the sample is read from reading output from the first photodetector.

2. The optical analyzer according to claim 1, wherein a final result of analysis of a same sample is provided based on a result of analysis of light emitted from the reading diode, reflected by or transmitted through the analysis disc and read by the first photodetector, and on a result of analysis of light emitted from the analyzing diode, reflected by or transmitted through the analysis disc and read by the first photodetector.

3. The optical analyzer according to claim 1, wherein the analyzing diode includes a plurality of analyzing diodes which emit laser beams having different wavelengths, and a final result of analysis of a same sample is provided based on a result of analysis of light emitted from one of the plurality of analyzing diodes, reflected by or transmitted through the analysis disc and read by the first photodetector, and on a result of light emitted from another analyzing diode among the plurality of analyzing diodes, reflected by or transmitted through the analysis disc and read by the first photodetector.

4. The optical analyzer according to claim 1, wherein the analyzing diode includes a plurality of analyzing diodes which emit laser beams having different wavelengths.

5. The optical analyzer according to claim 1, wherein the analyzing diode includes a plurality of analyzing diodes which emit laser beams having different wavelengths, and a final result of analysis of a same sample is provided based on a result of analysis of light emitted from one of the plurality of analyzing diodes and read by the photodetector at the position on the analysis disc at which the sample is read, and on a result of analysis of light emitted from another analyzing diode among the plurality of analyzing diodes and read by the photodetector at the position on the analysis disc at which the sample is read.

6. The optical analyzer according to claim 1, wherein the reading diode and the analyzing diode are provided in a single pick-up.

7. The optical analyzer according to claim 4, wherein if a plurality of samples are located in different positions in the direction of circumference of an analysis disc, the analyzing diodes are alternately selected and driven according to the positions of the samples.

8. The optical analyzer according to claim 4, wherein the analyzing diodes are alternately selected and driven while a same sample is being scanned.

9. The optical analyzer according to claim 4, wherein the analyzing diodes are alternately selected and driven every predetermined number of rotations of the analysis disc.

10. The optical analyzer according to claim 1, wherein switching between output from the reading diode and output from the analyzing diodes is made by reading a marker provided on the analysis disc.

11. The optical analyzer according to claim 1, comprising:
    a reading laser output driving unit driving the reading diode:
    an analyzing laser output driving unit driving the analyzing diode;
    a laser switching unit for selecting one of the reading diode and the analyzing diodes;
    a reading laser output monitoring unit monitoring laser emission from the reading diode;
    an analyzing laser output monitoring unit monitoring laser emission from the analyzing diode; and
    a laser output response measuring unit measuring, from output of each of the output monitoring units, a response time that elapses between a time point at which the reading laser output driving unit or the analyzing laser output driving unit starts driving and a time point at which a predetermined level of laser is emitted, wherein
    when switching between the reading diode laser emission and the analyzing diode laser emission is made, the laser output response measuring unit causes each laser output driving unit to start driving the next reading diode or analyzing diode to emit laser light in advance of an emission start time for the next reading diode or the analyzing diode by an amount of time equal to or close to the response time.

12. The optical analyzer according to claim 11, wherein the response time of a diode used for analysis is measured when the reading laser or the analyzing laser is driven.

13. The optical analyzer according to claim 11, wherein the reading laser output driving unit and the analyzing laser output driving unit apply a bias current to corresponding diodes thereof even while the diodes are not emitting laser.

14. The optical analyzer according to claim 2, wherein in a section in which an analyzing diode emits laser light, the optical pick-up is held at a position at which the reading diode emitted laser for the last time.

15. The optical analyzer according to claim 1, wherein the reading diode is used to obtain image data of the sample and the analyzing diode is used to obtain calorimetric data on the sample.

16. The optical analyzer according to claim 3, wherein the analysis is made by alternately selecting the wavelengths of laser light of the analyzing diodes every predetermined number of rotations of the analysis disc, or alternately selecting laser outputs of the plurality of diodes during a predetermined rotation of the analysis disc.

* * * * *